US008580988B2

(12) United States Patent
Hora et al.

(10) Patent No.: US 8,580,988 B2
(45) Date of Patent: Nov. 12, 2013

(54) BLOWN AND STRIPPED PLANT-BASED OILS

(75) Inventors: Michael John Hora, Marion, IA (US); Patrick Thomas Murphy, La Grange Park, IL (US)

(73) Assignee: Cargill, Incorporated, Wayzata, MN (US)

( * ) Notice: Subject to any disclaimer, the term of this patent is extended or adjusted under 35 U.S.C. 154(b) by 0 days.

(21) Appl. No.: 13/698,968

(22) PCT Filed: May 20, 2011

(86) PCT No.: PCT/US2011/037373
§ 371 (c)(1), (2), (4) Date: Nov. 20, 2012

(87) PCT Pub. No.: WO2011/146856
PCT Pub. Date: Nov. 24, 2011

(65) Prior Publication Data

US 2013/0066090 A1 Mar. 14, 2013

Related U.S. Application Data

(60) Provisional application No. 61/347,170, filed on May 21, 2010.

(51) Int. Cl.
*C11B 3/16* (2006.01)
*C07C 51/00* (2006.01)

(52) U.S. Cl.
USPC .......................................... 554/183; 554/167

(58) Field of Classification Search
USPC ................................................. 554/167, 183
See application file for complete search history.

(56) References Cited

U.S. PATENT DOCUMENTS

| | | | | |
|---|---|---|---|---|
| 1,790,464 | A | 1/1931 | Adams et al. | |
| 2,569,124 | A | 9/1951 | Christenson at al. | |
| 2,657,224 | A | 10/1953 | Bierke | |
| 4,330,625 | A | 5/1982 | Miller et al. | |
| 4,552,775 | A | 11/1985 | Baeling et al. | |
| 4,589,990 | A | 5/1986 | Zehler et al. | |
| 4,650,598 | A | 3/1987 | Roberts et al. | |
| 5,512,313 | A | 4/1996 | Cooper et al. | |
| 6,312,826 | B1 | 11/2001 | Shogren | |
| 6,443,661 | B1 | 9/2002 | Wathen | |
| 6,589,442 | B1 | 7/2003 | Wilson et al. | |
| 6,759,542 | B2 * | 7/2004 | Mahlum | 554/183 |
| 6,822,105 | B1 * | 11/2004 | Luxem et al. | 554/167 |
| 7,601,858 | B2 | 10/2009 | Cantrell et al. | |
| 7,608,729 | B2 | 10/2009 | Winsness et al. | |
| 7,989,647 | B2 | 8/2011 | Geiger et al. | |
| 8,008,516 | B2 | 8/2011 | Cantrell et al. | |
| 2004/0087808 | A1 | 5/2004 | Prevost et al. | |
| 2006/0107859 | A1 | 5/2006 | Sampei | |
| 2007/0004811 | A1 | 1/2007 | Bruner et al. | |
| 2007/0089356 | A1 | 4/2007 | Krasutsky et al. | |
| 2007/0260080 | A1 | 11/2007 | Lee et al. | |
| 2008/0190567 | A1 | 8/2008 | Winsness | |
| 2008/0299632 | A1 | 12/2008 | Winsness et al. | |
| 2009/0076913 | A1 | 3/2009 | Morgan | |
| 2009/0123609 | A1 | 5/2009 | Harris et al. | |
| 2009/0287007 | A1 | 11/2009 | Abraham et al. | |
| 2010/0036177 | A1 | 2/2010 | Ward | |

FOREIGN PATENT DOCUMENTS

| | | | |
|---|---|---|---|
| WO | 0162880 | A1 | 8/2001 |
| WO | 2007088421 | A2 | 8/2007 |
| WO | 2010135637 | A1 | 11/2010 |

OTHER PUBLICATIONS

Edgar S. Lower, "Blown (air oxidised) vegetable & marine oils & paint manufacture," Pigment and Resin Technology, May 1987, pp. 7-10.

N. Singh & M. Cheryan, "Extraction of Oil From Corn Distillers Dried Grains with Solubles," Transactions of the ASAE, 1998 American Society of Agricultural Engineers, vol. 41, pp. 1775-1777.

* cited by examiner

*Primary Examiner* — Deborah D Carr

(57) ABSTRACT

A method for producing a high viscosity, low volatiles blown stripped plant-based oil is provided. The method may include the steps of: (i) obtaining a plant-based oil; (ii) heating the oil to at least 90° C.; (iii) passing air through the heated oil to produce a blown oil having a viscosity of at least 50 cSt at 40° C.; (iv) stripping the blown oil from step (iii) to reduce an acid value of the blown oil to from 5 mg KOH/g to about 9 mg KOH/g; (v) adding a polyol to the stripped oil from (iv); and (vi) stripping the oil from step (v) to reduce the acid value of the oil to less than 5.0 mg KOH/g or less.

21 Claims, No Drawings

BLOWN AND STRIPPED PLANT-BASED OILS

CROSS REFERENCE TO RELATED APPLICATIONS

This application is a section 371 national-stage phase of International Application No. PCT/US11/37373, filed 20 May 2011, titled "BLOWN AND STRIPPED PLANT-BASED OILS", which claims priority to U.S. Application Ser. No. 61/347,170, filed 21 May 2010, titled "BLOWN AND STRIPPED PLANT-BASED OILS", which are hereby incorporated by reference in their entirety.

FIELD

The present disclosure relates to blown and stripped plant-based oils. In one particular embodiment, the disclosure relates to blown and stripped corn stillage oils. The disclosure also relates to methods for making such oils.

BACKGROUND

Lubricating and de-dusting oils historically have been made from petroleum feedstocks. These oils are typically designed for the application where they are to be utilized. Several of these applications require that the oil utilized be resistant to explosion and burning at high temperatures. Examples of applications where high temperature resistance is important include lubrication for metal forming processes, machine lubricants and de-dust oils for manufacturing processes, such as fiberglass insulation and stone wool insulation manufacturing.

Ethanol production from corn has increased in recent years. The corn is typically ground to a course powder that is then mixed with water and yeast and fermented to produce a fermented mixture (sometimes referred to as "mash") that contains residual solids, ethanol and other liquids. The other liquids include water, monoglycerides, diglycerides, triglycerides, glycerin, and free fatty acids. Typically, the liquid portion of the mash is heated to distill off the ethanol, which is captured and sold as an additive for automotive fuels.

The residual liquid remaining after the ethanol is removed contains free fatty acids and glycerol and from 1% to 3% by weight monoglycerides, diglycerides, triglycerides. The residual liquid from the distillation has generally been sold together with the solids portion of the mash as "distillers dry grain." The distillers dry grain generally is used as feed for livestock.

SUMMARY

In one embodiment, the plant-based oil is blown for a sufficient period of time at an appropriate temperature to produce highly polymerized oil. For example, air is blown (sparged) through the oil being maintained at a temperature of from 90° C. to 125° C. (preferably from 100° to 120° C. and more preferably from 105° C. to 115° C.) typically for from 20 to 60 hours (preferably from 24 to 42 hours). The resulting polymerized oil is then relatively heavily stripped. During the stripping, the blown oil typically is heated to a temperature from 230° C. to 270° C. (preferably from 235° to 245° C.) and vacuum stripped at a pressure of 100 torr or less, preferably 75 torr or less, and more preferably 50 torr or less for typically from 20 to 40 hours (preferably from 24 to 30 hours).

Typically, the oil is stripped to reduce the fatty acid content of the oil until the acid value of the oil is less than 5 mg KOH/gram, preferably about 3.5 mg KOH/gram or less, and in some instances about 3.0 mg KOH/gram or less, and further about 2.8 mg KOH/gram or less. In some instances where a particularly low acid value is beneficial (for example lube oil compositions), the oil preferably is stripped until the acid value is 1.0 mg KOH/gram or less, preferably 0.5 mg KOH/gram or less.

The inventors have surprisingly found that the use of a polyol (for example glycerol) can be utilized during the stripping to enhance the reduction of the fatty acid content of the blown, stripped plant-based oil to a desirably low level.

In one preferred aspect, the oil is stripped under vacuum until the acid value reaches from 5 mg KOH/gram to about 9 mg KOH/gram, preferably from about 7 mg KOH/gram to about 9 mg KOH/gram. Then sufficient polyol (preferably glycerin) is added to the oil to obtain a ratio of moles of hydroxyl groups added to fatty acid groups of typically from 1:5 to less than 1:1, preferably from 1:4 to 9:10, more preferably from 2:5 to 4:5, and further more preferably from 1:2 to 4:5. Where particularly low acid value is beneficial (for example, when the oil will be used in lube oil compositions), preferably sufficient polyol is added to provide a ratio of moles hydroxyl groups added to fatty acid of from 4:5 to 1:1. The vacuum is removed either prior to or soon after the polyol addition, preferably prior to the polyol addition. A slight nitrogen sparge is maintained through the oil to assist in the removal of any water or other volatile compounds from the oil. Preferably, the stripping is continued until the acid value of the oil is below 5.0 mg KOH/gram, and more preferably about 3.5 mg KOH/gram or less. In this aspect the final hydroxyl number of the blown, stripped plant-based oil is typically less than 50 mg KOH/gram, preferably less than 40 mg KOH/gram, and more preferably less than 30 mg KOH/gram, sometimes less than 25 mg KOH/gram. When the plant-based oil comprises corn stillage oil, the hydroxyl number is typically from about 23 to 29 mg KOH/gram. The viscosity of the blown, stripped plant-based oil is at least about 60 cSt at 40° C., preferably at least 150 cSt at 40° C. For high temperature applications, the viscosity is typically at least 500 cSt at 40° C., preferably at least 510 cSt at 50° C., and in some instances at least about 540 cSt at 40° C.

In an alternative aspect, a polyol (for example glycerin) is added to the oil at the beginning of the stripping step and the oil is stripped using a nitrogen sparge. In this aspect, a vacuum preferably is not applied to the oil and a nitrogen sparge of from 5 to 10 cubic feet per minute (cfm) typically is applied for every 45000 pounds mass of oil to be stripped. In this aspect more polyol is utilized, typically sufficient polyol (for example, glycerol) is added to provide a molar ratio of added hydroxyl groups to fatty acid groups of from 1:1 to 2:1, preferably from 1.6:1 to 1.9:1, and more preferably from 1.75:1 to 1.85:1. In this aspect, the stripping is continued until the acid value of the oil is below 5 mg KOH/gram, and preferably about 3.5 mg KOH/gram or less. In this aspect the final hydroxyl number of the blown, stripped plant-based oil is typically less than 50 mg KOH/gram, preferably less than 40 mg KOH/gram, and in some instances less than 30 mg KOH/gram and sometimes less than 25 mg KOH/gram. When the plant-based oil comprises corn stillage oil, the hydroxyl number is typically from about 23 to 29 mg KOH/gram. The viscosity of the blown, stripped plant-based oil is at least about 60 cSt at 40° C., preferably at least 150 cSt at 40° C. For relatively high temperature applications, the viscosity is typically at least 500 cSt at 40° C., preferably at least 510 cSt at 50° C., and in some instances at least about 540 cSt at 40° C.

In both the above aspects, high temperature applications, such as those that require a flash point of at least 293° C., and sometimes at least 296° C., for example at least 304° C., the weight loss of the blown, stripped corn stillage oil when measured using thermal gravimetric analysis ("TGA") at a temperature of from about 293° C. to 304° C. typically is less than 30 weight percent, sometimes less than 25 weight percent, preferably less than 20 weight percent and in some instances less than 15 weight percent. An example of the TGA procedures that can be used is the Noack Engine Oil Volatility (ASTM 5800-80) that has been modified for the appropriate temperature and duration as described below. The temperature and time utilized for measuring the weight loss of the blown, stripped corn stillage oil should be adapted based on the predicted temperature profile that the oil will be exposed to in the end-use application. For example, if the oil will be exposed to temperatures of about 293° C. to 296° C. for a period of 20 minutes to 45 minutes, then the TGA typically would be carried out at or slightly above the highest predicted operating temperature of 296° C. (for example 298° C.) and for a sufficient time to predict the behavior of the oil at the end-use operating temperature (for example for a period of at least 45 minutes). The weight lost during the TGA is proportional to the amount of volatiles that may be liberated in the end-use application. The inventors have surprisingly found that the blown, stripped corn stillage oils of the invention have much lower weight loss than typical petroleum-based oils under high temperature operating conditions.

The stripping reduces the content of free fatty acids and other volatiles. During the stripping process, the oil is also bodied. Typically, the final blown, stripped oil has a higher viscosity than the initial viscosity of the blown oil before stripping. The stripping also removes lower molecular weight glycerides and free fatty acids and unexpectedly produces a blown, stripped oil having a very high flash point. The blown, stripped oil can be used for end-use applications that require or take advantage of oils having high flash point. For example, the blown, stripped oils are particularly suitable for de-dusting fluids. "De-dusting fluids" are fluids used for reducing the dust created when a surface is agitated or perturbed. Examples of De-dusting fluids (De-dust oil) are oils that can be used to reduce the dust created during the manufacture of fiberglass and/or stone wool insulation. The stripped, blown-corn stillage oil will help minimize the chances of sparking and/or explosions in high flash point environments and will also degrade slower than petroleum based mineral oils having lower flash points. Typically, this blown, stripped plant-based oil has a flash point of at least 293° C., preferably at least 296° C., and more preferably at least 304° C., and in some instances at least 320° C.

In a particularly preferred aspect the plant-based oil comprises "corn stillage oil." As further described below, corn stillage oil is recovered from the residual material remaining after ethanol has been distilled from the fermentation of corn solids.

DETAILED DESCRIPTION

"Flash Point" or "Flash Point Temperature" is a measure of the minimum temperature at which a material will initially flash with a brief flame. It is measured according to the method of ASTM D-92 using a Cleveland Open Cup and is reported in degrees Celsius (° C.).

"Pour Point" or "Pour Point Temperature" is a measure of the lowest temperature at which a fluid will flow. It is measured according to the method of ASTM D-97 and is reported in degrees Celsius (° C.).

"Iodine Value" (IV) is defined as the number of grams of iodine that will react with 100 grams of material being measured. Iodine value is a measure of the unsaturation (carbon-carbon double bonds and carbon-carbon triple bonds) present in a material. Iodine Value is reported in units of grams iodine ($I_2$) per 100 grams material and is determined using the procedure of AOCS Cd Id-92.

"Hydroxyl number" (OH#) is a measure of the hydroxyl (—OH) groups present in a material. It is reported in units of mg KOH/gram material and is measured according to the procedure of ASTM E1899-02.

"Acid Value" (AV) is a measure of the residual hydronium groups present in a compound and is reported in units of mg KOH/gram material. The acid number is measured according to the method of AOCS Cd 3d-63.

"Gardner Color Value" is a visual measure of the color of a material. It is determined according to the procedure of ASTM D1544, "Standard Test Method for Color of Transparent Liquids (Gardner Color Scale)". The Gardner Color scale ranges from colors of water-white to dark brown defined by a series of standards ranging from colorless to dark brown, against which the sample of interest is compared. Values range from 0 for the lightest to 18 for the darkest. For the purposes of the invention, the Gardner Color Value is measured on a sample of material at a temperature of 25° C.

Plant-Based Oils

Plant-based oils are oils that are recovered from plants and algae. Plant-based oils that can be utilized in the invention include, soybean oil, canola oil, rapeseed oil, cottonseed oil, sunflower oil, palm oil, peanut oil, safflower oil, and corn stillage oil. Due to its relatively low polyunsaturation levels, relatively high mono- and di-unsaturation levels and other properties as further described below, the preferred plant oils utilized for the invention are corn stillage oil or blend of corn stillage oil with other oils, such as soybean oil. If a blend of corn stillage oil is utilized, the preferred oil to blend with corn stillage oil is soybean oil, due to its relatively higher level of polyunsaturates compared to corn stillage oil.

Corn Stillage Oil

The inventors have surprisingly discovered that the monoglycerides, diglycerides, triglycerides, free fatty acids, and glycerol (hereinafter collectively referred to as "corn stillage oil") can be recovered from the other residual liquids resulting from the distillation of dry-grind corn fermented mash by suitable means, preferably by centrifugation of the residual material remaining after the ethanol has been distilled off. Centrifugation typically recovers twenty five percent of the corn stillage oil originally present in the residual material being centrifuged.

The corn stillage oil recovered by centrifugation typically: has an acid value from 16 to 32 mg KOH/gram, preferably from 18 to 30 mg KOH/gram; has an iodine value from 110 to 120 g $I_2$/100 g sample; and contains from 0.05 to 0.29 percent by weight monoglycerides, from 1.65-7.08 percent by weight diglycerides, from 70.00 to 86.84 percent by weight triglycerides, from 8 to 16 percent by weight (for example, from 9 to 15 percent by weight) free fatty acids, and from 0.00 to 0.20 weight percent glycerin. Typically, the corn stillage oil has from 53 to 55 percent by weight groups derived from diunsaturated fatty acids, from 39 to 43 percent by weight groups derived from monounsaturated fatty acids, from 15 to 18 percent by weight groups derived from saturated fatty acids, and from 1 to 2 percent by weight groups derived from triunsaturated fatty acids. The groups derived from each of the above fatty acids are present either as groups within the mono-, di-, and tri-glycerides or as free fatty acids.

The free fatty acid content of the corn stillage oil most commonly is from about 11 to 12 percent (an acid value of from about 22 to 24 mg KOH/gram) is very high compared to conventional vegetable oils.

Recovery of Corn Stillage Oil

Fermented mash comprising ethanol, water, residual grain solids (including proteins, fats, and unfermented sugars and carbohydrates), and from 1 to 3 percent by weight corn stillage oil is heated to distill and recover ethanol from the fermented mash.

After the ethanol is distilled off, the remaining liquid portion typically contains from 1 wt % to 4 wt % corn stillage oil. The material remaining after the ethanol is distilled off is typically centrifuged using a centrifuge, such as a Westfalia sliding disk centrifuge available from Westfalia Corporation. From 25 wt % to 35 wt % of the corn stillage oil contained in the material is recovered during this centrifugation step. The recovered unprocessed corn stillage oil typically exhibits a Gardner color of 12 or greater, for example, a Gardner color of from 14 to 18.

Unprocessed corn stillage oil typically exhibits: a viscosity at 40° C. of from 25 to 35 cSt (for example from 28 to 31 cSt) as measured utilizing viscosity tubes in a constant temperature bath as further described below; a viscosity at 100° C. of from 5 to 10 cSt for example from 6 to 9 cSt as measured utilizing viscosity tubes in a constant temperature bath as further described below; a Viscosity Index of from 80 to 236 determined using the procedures and measurement scale established by the Society of Automotive Engineers; a flash point from 220° C. to 245° C., for example from 225° C. to 240° C.; a saponification value of from 170 to 206 mg KOH/g; a pour point typically of from −5° C. to −14° C.; an acid value of from 15 to 33 mg KOH/gram (for example, from 16 to 32 mg KOH/gram); an iodine value from 110 to 125 grams $I_2$/100 grams sample; and from 8 to 16 wt % (for example, from 9 to 15 wt %) free fatty acids.

Viscosity for this invention is measured according to the method of ASTM D445. In this method oil to be tested is placed in a calibrated glass capillary viscometer, which is then placed into a constant temperature bath at the temperature specified. Once thermal equilibrium is reached, the oil is drawn up into the reservoir of the capillary tube. As the fluid drains, it passes the top mark on the tube and a timer is started. When the oil passes the lower mark, the timer is stopped and the flow time is recorded. The recorded flow time is multiplied by a factor which is specific to each viscometer tube. The resultant product of the flow time multiplied by the factor is reported as viscosity in cSt at the test temperature.

Unprocessed corn stillage oil also typically contains two phases at 25° C. The first phase is the liquid phase, which settles toward the top of any container that contains the corn stillage oil. This phase typically is reddish in color. The second phase is a solid that typically settles toward the bottom of any container containing the oil. At 62° C., the second phase tends to dissolve into the liquid phase, but will settle out again if the untreated corn stillage oil is cooled to room temperature. The inventors have determined that the second solid phase typically makes up at least 4 percent by weight (4 wt %) of the total unprocessed corn stillage oil. For example, the second solid phase may make up from 5 wt % to 12 wt % of the unprocessed corn stillage oil. For purposes of this invention, this second solid phase is referred to as the "titre."

Blowing the Plant-Based Oil

The blowing typically is achieved by sparging air through the plant-based oil that has been heated to from 90° C. to 125° C., preferably from 100° C. to 120° C., and more preferably from 105° C. to 115° C. The vessel containing the plant-based oil during the blowing step typically is at atmospheric pressure. The pressure of the air being sparged through the oil is generally high enough to achieve the desired air flow through the plant-based oil. The air is introduced at a sufficient flow rate for a sufficient period of time to achieve the desired viscosity. Typically, the air is introduced into the plant-based oil at a rate of 0.009 to 0.011 cubic feet per minute per pound of oil present. Preferably, the air is dispersed evenly in the vessel to maximize surface area exposure. Typically the vessel will have a distribution ring or spoke-like header to create small volume bubbles evenly within the oil. The duration of sparging air through the oil is varied and determined according to the desired properties of the blown oil and the end-use applications for the resulting product.

Air is blown through the plant-based oil to provide blown-oil which advantageously has a relatively high level of polymerization, as shown by increased viscosities at 40° C. (typically above 50 cSt@40° C. preferably above 60 cSt@40° C. more preferably above 130 cSt@40° C., and further more preferably above 200 cSt@40° C., and where high molecular weight is particularly desirable, above 2500 cSt@40° C. and in some instances 5000 cSt@40° C.

When corn stillage oil is utilized, surprisingly, the acid value for the blown corn stillage oil is not significantly increased compared to the acid value for the unblown corn stillage oil. Typically the acid value does not increase when corn stillage oil is blown. Preferably, the blown corn stillage oil comprises relatively no more than 10 relative percent more free fatty acids than the starting unblown corn stillage oil, and more preferably, the free fatty acid content of the blown corn stillage oil is equivalent to or slightly less than the free fatty acid content of the starting corn stillage oil.

The fact the free fatty acid content of blown corn stillage oil is not significantly higher than the free fatty acid value for the starting unblown corn stillage oil is unexpected because the acid value for other vegetable oils, such as soybean oil, does increase significantly when the oil is blown. For example, a sample of soybean oil with an acid value of less than 0.1 mg KOH/g when blown to a viscosity of 130 cSt@40° C. typically has an acid value of 3 to 6 mg KOH/gram, or more. Generally, the acid value of a vegetable oil increases significantly when air is blown into the oil at temperatures above 100° C.

For plant-based oils other than corn stillage oils, the acid value of a plant-based oil increases significantly when air is blown into the oil at temperatures above 100° C. For blends of corn-stillage oil with other oils, the acid value will typically stay the same or decrease during the blow. Typically, for a blend of corn stillage oil and soybean oil having a weight ratio of corn stillage oil to soybean oil from about 1:2 to 3:1, the acid value after the blown blend has reached a viscosity of about 200 cSt at 40° C. is from about 7 to 10 mg KOH/gram for the 1:2 blend to about 13 to 15 mg KOH/gram for the 3:1 blend. The amount of increase will be proportional to the starting acid value of the blend and the ratio of corn stillage oil to soybean oil.

The reactions that occur during the blowing of the oil increase the molecular weight of the oil, which tends to increase the viscosity of the blown oil versus the unblown oil. Additionally, the blowing process introduces hydroxyl functionality onto the resulting oil, which also tends to increase the viscosity of the oil. The blown-corn stillage oil typically has a hydroxyl number from 8 to 60 mg KOH/gram oil. The higher viscosity (especially at higher temperature) provides the oil with better hydrodynamic lubrication properties.

For high-flash point end-use applications (as described below) for example, high temperature de-dust applications, asphalt modifiers and open gear lubricants applications, the blowing is continued for a time sufficient to obtain a plant-based oil having a viscosity of: at least 200 cSt at 40° C., preferably at least 300 cSt at 40° C., and in some instances at least 1500 cSt at 40° C.; this will provide for an oil having a viscosity of: at least 500 cSt at 40° C., preferably at least 700 cSt at 40° C., and more preferably at least 730 cSt at 40° C., and in some instances at least 5000 cSt at 40° C. after stripping as described, below.

With even dispersion and small volume air bubbles, air typically is sparged through the oil for from 30 to 40 hours (when the oil is at a temperature of from 105° C. to 115° C. at atmospheric pressure, at the rates described above, to achieve these desired viscosities.) Longer sparging times typically will be necessary if the air is not evenly dispersed within the oil and/or the volume of the air bubbles are relatively larger.

Optionally, a catalyst may be used in some embodiments to enhance the blowing of the oil. Examples of catalysts that may be useful include peroxides, and catalysts comprising metals selected from the group consisting of Transition Elements and Group IV metals as described in "McGraw-Hill Dictionary of Scientific and Technical Terms," Appendix 7 (Fifth Edition 1994).

Further examples of catalysts that may be useful for enhancing the blowing procedure include catalysts comprising metals related from the group consisting of: tin, cobalt, iron, zirconium, titanium and combinations thereof.

Stripping of the Plant-Based Oil

The blown plant-based oil can be stripped using several methods. Examples of methods that may be utilized to strip the oil of unwanted volatile compounds include vacuum stripping and nitrogen stripping (i.e. sparging nitrogen through the blown oil).

Typically, the temperature during the stripping of the oil is from 230° C. to 270° C., preferably from 235° C. to 245° C. As discussed earlier, the stripping will typically increase molecular weight and therefore raise the viscosity of the oil. The stripping will also lower the content of free fatty acids in the oil and therefore reduce the acid value of the resulting stripped oil.

In a first preferred aspect, the blown plant-based oil typically is stripped in two stages. During the initial stripping stage or phase, the plant-based oil preferably is vacuum stripped. During this initial vacuum stripping the pressure on the vapor duct between the reactor and condenser typically is less than 100 torr, preferably less than 75 torr, more preferably less than 50 torr, further more preferably less than 35 torr, and most preferably 20 torr or less. During this initial vacuum stripping stage, the oil is typically lightly sparged with nitrogen gas to assist in the removal of volatiles. The nitrogen preferably is introduced at a rate high enough to assist in removal of the volatiles, but low enough to not prevent the pulling of a vacuum on the oil. In this first aspect, the initial stripping phase may be conducted by applying a nitrogen sparge on the oil, without the use of a vacuum. If no vacuum is applied, the nitrogen preferably is sparged at a rate of from about 25 cubic feet per minute (cfm) to about 60 cfm through the oil per 45000 pounds mass of oil present.

The inventors have surprisingly discovered that when it is necessary to reduce the acid value to particularly low levels (for example to values of 3.5 mg KOH/gram or less), it may be preferable to optionally add small amounts of a polyol to the blown oil being stripped.

During the first preferred aspect, the blown oil is stripped using nitrogen or vacuum stripping until the acid value of the oil is reduced to from 5 mg KOH/gram to about 9 mg KOH/gram, preferably from about 7 mg KOH/gram to about 9 mg KOH/gram. Then the polyol, preferably glycerin is added to the oil and the oil is stripped through nitrogen sparging until the acid value of the oil is less than 5.0, preferably until the acid value is 3.5 mg KOH/gram or less, and in some instance 3.0 mg KOH/gram or less or 2.8 mg KOH/gram or less. During this final stripping stage, a nitrogen sparge preferably is maintained on the oil to assist in the removal of volatiles from the oil, including water that may be liberated by the reaction of glycerin with fatty acids. However, during this final stripping state a vacuum preferably is no longer maintained on the vessel containing the oil. Once the acid value has been reduced to the desired value, the heat may be removed if the desired viscosity has been obtained. If the desired viscosity has not been reached, the oil will continue to be heated until the desired value for viscosity is obtained. After the desired acid value and viscosity have been obtained, the blown, stripped plant-based oil is allowed to cool. The hydroxyl number of the stripped plant-based oil typically is less than 50 mg KOH/gram, preferably less than 40 mg KOH/gram, more preferably less than 30 mg KOH/gram, and in some instances less than 25 mg KOH/gram.

The amount of polyol added to the blown oil in this first preferred aspect typically is sufficient to obtain a ratio of moles of from 1:5 to less than 1:1, preferably from 1:4 to 9:10, more preferably from 2:5 to 4:5, and further more preferably from 1:2 to 4:5.

In a second preferred aspect, the polyol is added at the beginning or soon after stripping of the blown oil has commenced. In this second preferred aspect, the temperature of the oil is as described above. Typically, sufficient polyol (preferably glycerin) is added to the blown oil to obtain a ratio of moles of hydroxyl groups added per mole of fatty acids groups present in the oil of from about 1:1 to about 2:1, preferably from about 1.6:1 to about 1.9:1, and more preferably from about 1.75:1 to about 1.85:1. During this aspect, nitrogen is sparged through the oil, typically at a rate of from about 5 to 10 cfm per 45,000 pounds mass oil. Preferably, during this aspect a vacuum is not applied to the oil. Nitrogen is sparged through the oil until the acid value of the oil is less than 5 mg KOH/gram, preferably less than 3.5 mg KOH/gram and in some instances 3.0 mg KOH/gram and even 2.8 mg KOH/gram. Once the acid value has been reduced to the desired value, the heat may be removed if the desired viscosity has been obtained. If the desired viscosity has not been reached, the oil will continue to be heated until the desired value for viscosity is obtained. After the desired acid value and viscosity have been obtained, the blown, stripped plant-based oil is allowed to cool.

Stripping the oil increases the viscosity of the resulting oil compared to the non-stripped oil and will increase the flash point of resulting oil. If the first aspect described above is utilized to strip the oil, it typically takes a stripping time of from about 20 to about 30 Hours (preferably from about 24 to about 27 hours) to obtain an acid value of less than 5.0 mg KOH/gram and a viscosity of at least 500 cSt at 40° C. (preferably an acid value of about 3.5 mg KOH/gram or less and a viscosity of at least 520 cSt at 40° C.). If the second aspect described above is utilized to strip the oil, it typically takes a stripping time of from about 16 to about 24 Hours (preferably from about 18 to about 20 hours) to obtain an acid value of less than 5.0 mg KOH/gram and a viscosity of at least 500 cSt at 40° C. (preferably an acid value of about 3.5 mg KOH/gram or less and a viscosity of at least 520 cSt at 40° C.).

Surprisingly, the addition of the polyol to the blown oil does not adversely affect the properties of the blown stripped oil; and a blown stripped plant-based oil having a high viscosity and high flash point is produced. Typically, the hydroxyl number is less than 50 mg KOH/gram, preferably less than 40 mg KOH/gram, more preferably less than 30 mg KOH/gram, and in some instances less than 25 mg KOH/gram.

Polyol

As discussed above, the inventors have surprisingly discovered that by adding a polyol to the blown oil the blown oil may be more readily stripped to obtain a blown, stripped plant-based oil (such as a corn stillage oil) having a high viscosity (for examples at least 500 cSt at 40° C., preferably at least 520 cSt at 40° C.) and a low acid value as described above, which will result in a blown, stripped plant-based oil having a high flash point.

The added polyol preferably has a molecular weight of at least 80 Daltons, more preferably at least 85 Daltons, and more preferably at least 90 Daltons. In order to aid in the reaction of the polyol with the free fatty acids, the polyol preferably has a hydroxyl of at least 200 mg KOH/gram, preferably at least 1000 mg KOH/gram. Preferably, the polyol has at least two hydroxyl groups per molecule, and more preferably at least 3 hydroxyl groups per molecule. The polyol preferably has a boiling point of at least 250° C., more preferably at least 270° C., and further more preferably at least 285° C. Any reference to boiling point herein means the boiling point at a pressure of 760 mm Hg. Due to its relatively high molecular weight (92 Daltons), relatively high boiling point (290° C.), high number of hydroxyl groups per molecule (3), and ready commercial availability, glycerin is the preferred polyol to utilize in the invention.

Examples of other polyols that may be utilized include, but are not limited to, trimethylol propane ("TMP"), polyethylene glycol ("PEG"), pentaerythritol, and polyglycerol.

In certain preferred aspects of the invention, the polyol (e.g. glycerol) contains less than 500 ppm chloride ions. In certain aspects, the polyol contains less than 300 ppm, less than 200 ppm, less than 100 ppm, less than 70 ppm, or less than 50 ppm chloride ions. Reduced chloride ion concentrations may minimize corrosion concerns in products that are manufactured utilizing a blown, stripped plant-based oil of the present invention. In one particularly preferred aspect, the polyol comprises technical grade or USP glycerol, typically having less than 30 ppm chloride ions and preferably less than 20 ppm chloride ions (for example less than 10 ppm chloride ions).

End-Use Applications

High-Flash Point Applications

High flash point applications often expose lubricating and process oil to temperatures above 260° C., often above 287° C. and in some instance temperature up to and/or above 315° C. Petroleum-based oils generally do not have flash point temperatures high enough to safely operate in this type of environments. Also, the petroleum-based oils may break down and rapidly oxidize and in a worse case scenario may burn in these types of environments. The inventors have surprisingly found that by heavily blowing the plant-based oil, such as corn stillage oil the molecular weight and viscosity can be increased sufficiently to be able to operate effectively in end-use applications requiring such high flash points once the resulting blown has been stripped to reduce the acid value to 3.5 mg KOH/g or less, preferably 3.0 mg KOH/g or less, and more preferably 2.8 mg KOH/g or less.

Examples of suitable applications for the blown, stripped plant-based oil include de-dusting fluids that require a flash point of at least 293° C., preferably at least 296° C., and more preferably at least 304° C., and in some instances at least 320° C.

The blown, stripped, plant-based oil will help minimize the chances of sparking and/or explosions in high flash point environments and will also degrade slower than petroleum based mineral oils having lower flash points.

Typically, the high-flash point blown, stripped plant-based oil typically also exhibits a pour point of lower than 0° C., preferably lower than negative 5° C. This combination of high flash point and relatively low pour point is unexpected and is believed to result from the blown, stripped plant-based oil (such as corn stillage oil) having a relatively narrow molecular weight distribution with completely randomized molecular structures compared to petroleum base oils. This provides an oil that remains flowable at relatively low temperatures, while still exhibiting good viscosity and lubrication at high temperatures and a high flash point, as described above.

Examples of additional end-use applications that require such high flash points oils and fluids include, but are not limited to: asphalt modification, forging lubricants, high temperature fluids used for stabilization of sand molds for casting metal and high temperature bearing lubrication. Examples of applications where the blown, stripped plant-based oils (such as blown, stripped corn stillage oils) of this invention are advantageous include applications where high temperature De-dusting fluids are utilized, such as in the manufacture of fiberglass insulation and stone wool insulation applications.

EXAMPLES

The following examples are presented to illustrate the present invention and to assist one of ordinary skill in making and using the same. The examples are not intended in any way to otherwise limit the scope of the invention.

Example 1

Production of Vacuum Distilled Corn Stillage Oil

The vacuum distilled corn stillage oil of example 1 is made according to the ICM Process. This process exposes the fermented corn mash to temperatures of about 82.2° C. under a vacuum from about 50 to about 300 torr to distill off ethanol. The corn stillage oil is recovered by centrifuging the materials remaining after the distillation to recover the vacuum distilled corn stillage oil. The properties of the vacuum distilled corn stillage oil is set forth below in Table 2. While not measured, the vacuum distilled corn stillage oil is believed to contain from about 5 to about 12 percent by weight titre.

TABLE 2

Properties of Vacuum Distilled Corn Stillage Oil

| | Sample No. 2-1 |
|---|---|
| 40° C. Viscosity (cSt) | 31 |
| 100° Viscosity (cSt) | 8 |

TABLE 2-continued

| Properties of Vacuum Distilled Corn Stillage Oil | Sample No. 2-1 |
|---|---|
| Viscosity Index | 249 |
| Flash Point (° C.) | 238 |
| Saponification Value (mg KOH/g) | 202 |
| Pour Point Temperature (° C.) | −7 |
| Acid Value (mg KOH/grams) | 22.2 |
| Free Fatty Acid (wt %) | 11.1 |
| Iodine value (gram $I_2$/100 grams) | 122 |
| Gardner Color | 15 |
| Hydroxyl number (mg KOH/gram) | 9 |

Example 1a

Production of Pressure Distilled Corn Stillage Oil

The pressure distilled corn stillage oil of example 1a is made according to the Delta T Process. In this process the fermented corn mash is exposed to temperatures of about 235° F. to 250° F. at pressures of from about 1 psig to about 15 psig to distill off ethanol. The pressure distilled corn stillage oil is recovered by centrifuging the material remaining after the distillation to recover the pressure distilled corn stillage oil. The properties of the pressure distilled corn stillage oil is set forth below in Table 2a. While not measured, the pressure distilled corn stillage oil is believed to contain from about 5 to about 12 percent by weight titre.

TABLE 2a

| Properties of Pressure Distilled Corn Stillage Oils | Sample No. 2-1a |
|---|---|
| 40° C. Viscosity (cSt) | 31 |
| 100° Viscosity (cSt) | 8 |
| Viscosity Index | 249 |
| Flash Point (° C.) | 238 |
| Saponification Value (mg KOH/g) | 202 |
| Pour Point Temperature (° C.) | −7 |
| Acid Value (mg KOH/gram) | 23 |
| Free Fatty Acid (wt %) | 11.5 |
| Iodine value (gram $I_2$/100 grams) | 118 |

TABLE 2a-continued

| Properties of Pressure Distilled Corn Stillage Oils | Sample No. 2-1a |
|---|---|
| Gardner Color | 16 |
| Hydroxyl number (mg KOH/gram) | 9 |

Example 2

Blowing the Corn Stillage Oil in Smaller Reactor

Into a 2000 milliliter glass reactor equipped with a stirrer, a heating mantel, a temperature regulator and air blowing tubes, 1200 grams of corn stillage oil, as indicated in Table 3, is charged. The corn stillage oil is heated to the temperatures indicated in Table 3. Air is sparged through the oil as it is heated. The air is sparged through the oil at a rate that maximizes the rate while at the same time causes a relatively even distribution of air bubbles within the oil. The rate of sparging is generally limited by the volume of the reactor. The speed with which viscosity increases is directly proportional to the rate at which air is being blown into the corn stillage oil, and indirectly proportional to the size of the air bubbles. The smaller the air bubbles, the more surface area the faster the reaction. The oil within the reactor is tested periodically to determine the viscosity at 40° C. of the blown oil. When the desired viscosity is obtained, the air sparging is stopped and the reactor is allowed to cool. Air is sparged through each of the samples for the times indicated in Table 3. The properties of the resulting blown oils (Samples 3-1 through 3-3) are set forth in Table 3.

Example 2a

Blowing the Corn Stillage Oil in a Larger Size Reactor

Into a 6000 gallon steel tank equipped with an air sparge distributor, positive displacement blower, regenerative thermal oxidizer (RTO) system, controlled heat source (whether it be external steam or hot oil jacket), and cooling coils, 45,000 pounds of corn stillage oil, as indicated in Table 3 is charged. Air is sparged through the oil as it is heated. The air is sparged through the oil at a rate that maximizes the rate while at the same time causes a relatively even distribution of air bubbles within the oil. The rate of sparging is set so the reactor remains under a slight vacuum which indicates the RTO system can remove VOCs adequately and safely as they are produced from the reaction. The speed with which viscosity increases is directly proportional to the rate at which air is being blown into the corn stillage oil, and indirectly proportional to the size of the air bubbles. The smaller the air bubbles, the more surface area the faster the reaction. The oil within the reactor is tested periodically to determine the viscosity at 40° C. of the blown oil. When the desired viscosity is obtained, the air sparging is stopped and the reactor is allowed to cool. Air is sparged through each of the samples for the times indicated in Table 3. The properties of the resulting blown oil (Sample No. 3-4) is set forth in Table 3.

TABLE 3

| Properties of Blown Corn Stillage Oil | | | | |
|---|---|---|---|---|
| | Sample No. | | | |
| | 3-1 | 3-2 | 3-3 | 3-4 |
| Corn Stillage Oil Used | Sample 2-1 | Sample 2-1 | Sample 2-1 | Sample 2-1 |
| Sparging Temperature (° C.) | 105 | 105 | 250 | 115 |
| Sparging Time (hours) | 23.5 | 42.5 | 14.5 | 42 |
| Viscosity@40° C. (cSt) | 63 | 220 | 526 | 210 |
| 100° Viscosity (cSt) | 12 | 34.7 | 56 | |
| Viscosity Index | 192 | 206 | 173 | |
| Flash Point (° C.) | 284 | 277 | 295 | |
| Saponification Value (mg KOH/gram) | 190 | 200 | 192 | |
| Pour Point Temp (° C.) | −9 | −9 | −4 | |
| Acid Value (mg KOH/gram) | 21 | 23 | 21 | 18 |
| Free Fatty Acid (wt %) | 10.5 | 11.5 | 10.5 | 9 |
| Iodine value (gram $I_2$/100 grams) | 120 | 102 | 83 | |
| Gardner Color | 6 | 6 | >18 | 7 |
| Hydroxyl number (mg KOH/gram) | 9 | 53 | 43 | 55 |

As can be seen from Table 3, varying the time period and temperature of the corn stillage oil during air sparging results in blown corn stillage oil having varying viscosities. The time required for blowing the corn stillage oils of Samples 3-1 and 3-2 is relatively high, due to the large volume air bubbles utilized and the uneven dispersion of air bubbles within the reactor. A higher temperature was utilized to sparge Sample 3-3 to reduce the sparging time. When air is dispersed more evenly into the oil and the volume of the air bubbles are smaller, the time to manufacture a blown corn stillage oil at a lower temperature (for example from 100° C. to 120° C.) is greatly reduced. For example, Sample 3-4 exhibits almost twice the viscosity of Sample 3-2, but took about the same amount of time to produce. It is believed this results from better distribution of the air bubbles and relatively smaller size air bubbles produced in the larger sae reactor.

In addition, while not measured, the blown corn stillage oils of Table 3 are believed to contain less than one percent by weight titre.

Example 3

Stripping the Blown Corn Stillage Oil Using a Large Size Stripping Reactor

Into a 6000 gallon stainless steel reactor equipped with a mechanical agitator, a nitrogen sparge distributor, vacuum pump, regenerative thermal oxidizer (RTO) system, controlled heat source(hot oil jacket), and cooling coils, 45,000 pounds of blown corn stillage oil from example 2, as indicated in Table 4, is charged. Nitrogen is sparged at about 5-10 CFM through the oil as it is heated to about 235° C. to 245° C. Once the oil reaches the desired temperature, shut off nitrogen sparge and apply full vacuum to the reactor (preferred pressure of 20 torr or less). The oil within the reactor is tested periodically to determine the viscosity at 40° C., flash point, and the acid value of the oil. When the oil reaches acid value of from 7-9 mg KOH/gram, break the vacuum to atmospheric pressure. Add desired amount of USP grade glycerol (which has lower than 0.3 weight percent impurities and less than or equal to 10 PPM $Cl^-$) to the oil in the reactor and continue nitrogen sparging at while maintaining the temperature 235° C.-245° C. at atmospheric pressure until acid value is less than 5.0 and preferably less than 3.5 mg KOH/gram. When the desired viscosity, flash point, and acid value are obtained, cool the reactor. The oil samples are reacted for the times indicated in Table 4. The properties of the resulting stripped oils are set forth in Table 4.

TABLE 4

| Properties of Stripped Blown Corn Stillage Oil | | | |
|---|---|---|---|
| | Sample No: | | |
| | 4-1 | 4-2 | 4-3 |
| Blown corn stillage oil used | Sample 3-4 | Sample 3-4 | Sample 3-4 |
| Glycerol Addition (% wt) | 0 | 0.15 | 1.2 |
| Glycerol Hydroxyl number (mg KOH/gram) | N/A | 1800 | 1800 |
| Reaction time (hours) | 36 | 27 | 20 |
| Final Acid Value (mg KOH/gram) | 3.6 | 2.7 | 2.2 |
| Hydroxyl number (mg KOH/gram) | 29 | 19 | 37 |
| Molar Ratio of OH— added/ fatty acid group present before addition | N/A | 0.77:1 | 1.8:1 |
| Flash Point by Cleveland Open Cup Method ° C. | 315 | 326 | 316 |
| Viscosity @ 40° C. (cSt) | 580 | 465 | 531 |
| GPC Data (relative wt %) | | | |
| Mn | 1938 | 1876 | |
| Total FA + FAME (wt % Fatty Acid/Fatty Acid Methyl Ester) | 0.73 | 0.87 | 1.9 |
| Diglyceride | 8.41 | 10.68 | 15.22 |
| Monomer | 24.03 | 23.14 | 21.13 |
| Dimer | 17.34 | 15.63 | 17.06 |
| Trimer | 8.37 | 7.68 | 8.48 |
| Tetramer+ | 41.11 | 42 | 35.83 |

As can be seen from Table 4, varying the amount of polyol added to the corn stillage oil during stripping results in varying batch times. The more glycerol (a polyol) used, the shorter the batch time. As can be seen from Samples 4-2 and 4-3, the addition of polyol in small amounts and low molar ratios of OH— groups added to fatty acid groups present in the oil does provide blown, stripped corn stillage oils having a higher flash point due to the lower acid value versus Sample 4-1 where no polyol (glycerol) is added. In general, a lower acid value equates to a higher flash point. However, as becomes apparent when comparing the GPC analysis of Sample 4-3 to Samples 4.1 and 4.2, using more polyol induces more random interesterification which creates more small, undesirable molecules like diglycerides. This action also breaks up some of the desirable high molecular weight molecules like tetramers and larger. As can be seen from this Example, the molar ratio of OH-groups added to fatty acid present in the oil before addition (just prior to addition of glycerol) preferably is from is from 1:5 to less than 1:1, preferably from 1:4 to 9:10, more preferably from 2:5 to 4:5, and further more preferably from 1:2 to 4:5, when it is desirable to maximize the molecular weight of the resulting blown, stripped oil and to minimize the hydroxyl number of the resulting blown, stripped oil.

What is claimed is:

1. A method for producing a high viscosity, low volatiles blown stripped plant-based oil, the method comprising the steps of:

(a) obtaining a plant-based oil;

(b) heating the oil to at least 90° C.;

(c) passing air through the heated oil to produce a blown oil having a viscosity of at least 50 cSt at 40° C.;

(d) stripping the blown oil from step (c) to reduce an acid value of the blown oil to from 5 mg KOH/g to about 9 mg KOH/g; and (e) adding a polyol to the stripped oil from (d); and (f) stripping the oil from step (e) to reduce the acid value of the oil to less than 5.0 mg KOH/g or less.

2. The method of claim 1 wherein the oil resulting from step (f) exhibits a viscosity at 40° C. of at least 150 cSt.

3. The method of claim 1, wherein the oil resulting from step (f) exhibits: a viscosity at 40° C. of at least 500 cSt; an acid value of 4 mg KOH/gram or less; a hydroxyl number of less than 50 mg KOH/gram; and a flash point of at least 293° C., in particular aspects, a flash point of at least 296° C.

4. The method of claim 1 wherein a catalyst comprising a peroxide or a metal selected from the groups consisting of Transition Elements and Group IV is added to the oil prior to or during step (c).

5. The method of claim 1 wherein a catalyst is added to the oil prior to or during step (c), the catalyst comprising a metal selected from the group consisting of: tin, cobalt, iron, zirconium, titanium, and combinations thereof.

6. The method of claim 1 wherein the polyol added comprises glycerin, and sufficient glycerin is added to obtain a molar ratio of added hydroxyl group to fatty acid groups present in the oil resulting from step (d) is from about 1:5 to less than about 1:1, in particular aspects, from about 2:5 to about 8:10.

7. The method of claim 1 wherein the plant-based oil of step (a) is selected from the group consisting of: soybean oil, sunflower oil, safflower oil, canola oil, rapeseed oil, cottonseed oil, corn oil, corn stillage oil and mixtures thereof.

8. The method of claim 1 wherein the plant-based oil of step (a) comprises corn stillage oil having an initial acid value from about 12 to about 34 mg KOH/gram, preferably from about 16 to about 32 mg KOH/gram.

9. A method for producing a high viscosity, low volatiles blown, stripped, corn stillage oil, the method comprising the steps of:

(a) obtaining a corn stillage oil having an initial acid value of from about 12 mg KOH/gram to about 34 mg KOH/gram;

(b) heating the oil to at least 90° C.;

(c) passing air through the heated to produce a blown-corn stillage oil;

(d) stripping the blown-corn stillage oil to reduce the acid value of the blown-corn stillage oil from about 6 mg KOH/gram to about 9 mg KOH/gram;

(e) adding a sufficient amount of glycerin to the stripped oil from (d) to obtain a molar ratio of hydroxyl groups from the added glycerin to the free fatty acids present in the oil from (d) of from about 1:5 to less than 1:1; and (f) stripping the oil from step (e) to produce a blown, stripped corn stillage oil having a hydroxyl number less than about 50 mg KOH/gram and a final acid value of 3.5 mg KOH/gram or less.

10. The method of claim 9, wherein sufficient glycerin is added to obtain a molar ratio of hydroxyl groups from the added glycerin to the free fatty acids present in the oil from (d) of from about 1:4 to about 9:10.

11. The method of claim 9, wherein sufficient glycerin is added to obtain a molar ratio of hydroxyl groups from the added glycerin to the free fatty acids present in the oil from (d) of from about 2:5 to about 4:5.

12. The method of claim 9 wherein the oil resulting from step (f) has a flash point of at least 293° C.

13. The method of claim 9 wherein, the oil resulting from step (f) has a flash point of at least 296° C. and exhibits a viscosity of at least 680 cSt at 40° C.

14. The method of claim 9 wherein the oil from step (f) has a flash point of at least 310° C.

15. A method for producing a high viscosity blown, stripped plant-based oil, the method comprising the steps of:

(a) obtaining a plant-based oil;

(b) heating the oil to at least 105° C.;

(c) passing air through the heated oil to produce a blown plant-based oil having a viscosity of at least 50 cSt at 40° C.;

(d) adding a polyol to blown plant-based oil from step (c); and (e) stripping the blown oil from step (d) to reduce an acid value of the blown oil to less than 5.0 mg KOH/gram.

16. The method of claim 15, wherein the plant-based oil comprises a corn stillage oil and the blown oil resulting from step (c) has a viscosity of at least 1500 cSt at 40° C.

17. The method of claim 15 wherein the polyol exhibits a boiling point of at least 250° C. and has a hydroxyl number of at least 200 mg KOH/gram.

18. The method of claim 15 wherein the polyol exhibits a boiling point of at least 270° C. and is selected from the group consisting of polyglycerol, trimethylol propane, glycerin, polyethylene glycol, pentaerythritol, and mixtures thereof.

19. The method of claim 15 wherein the polyol comprises glycerin.

20. The method of claim 15 wherein sufficient polyol is added to obtain a molar ratio of hydroxyl groups added to free fatty acid groups of from about 1:1 to about 2:1.

21. The method of claim 15, wherein the blown plant-based oil has a viscosity of at least 200 cSt at 40° C.

* * * * *